United States Patent [19]

Pincon

[11] 4,214,962
[45] Jul. 29, 1980

[54] ACTIVATED OXYGEN PRODUCT AND WATER TREATMENT USING SAME

[76] Inventor: Andrew J. Pincon, 1819 Grand Ave., Chicago, Ill. 60602

[21] Appl. No.: 927,140

[22] Filed: Jul. 21, 1978

Related U.S. Application Data

[63] Continuation-in-part of Ser. No. 645,363, Dec. 30, 1975, Pat. No. 4,124,467.

[51] Int. Cl.² .......................... A61L 1/00; B01J 1/00; B01J 1/10; C02B 3/08
[52] U.S. Cl. ..................... 204/157.1 R; 204/157.1 H; 250/527; 210/632; 422/23; 422/24; 422/186
[58] Field of Search ................. 204/157.1 R, 157.1 H; 21/54 R, 74 A, 102 A, DIG. 2; 250/527; 210/632; 422/23, 24, 186

[56] References Cited

U.S. PATENT DOCUMENTS

| 3,659,096 | 4/1972 | Kompanek | 422/22 |
| 3,977,952 | 8/1976 | Knoevenagel et al. | 204/157.1 R |
| 4,045,316 | 8/1977 | Legan | 204/157.1 R |

FOREIGN PATENT DOCUMENTS 48-34677  10/1973  Japan ............................. 204/157.1 H

*Primary Examiner*—Howard S. Williams
*Attorney, Agent, or Firm*—Jones, Thomas & Askew

[57] ABSTRACT

An activated oxygen product produced by irradiating oxygen with electromagnetic radiation of wavelength less than 200 nanometers, and having an unusually high oxidation potential and unique spectral properties. The product may be used to treat water in order to reduce surface tension, oxidize wastes, reduce manganous ion concentration, and disinfect water without creating carcinogens.

14 Claims, 7 Drawing Figures

U.S. Patent Jul. 29, 1980 Sheet 1 of 3 4,214,962
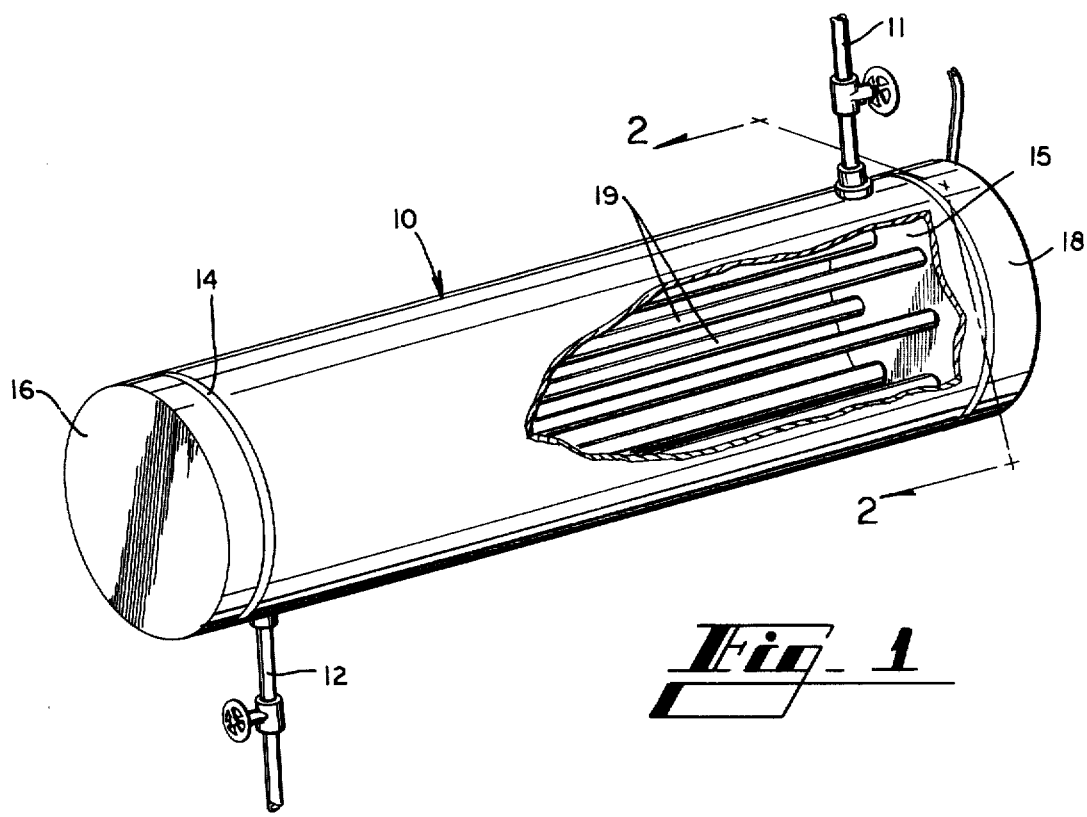
Fig. 1
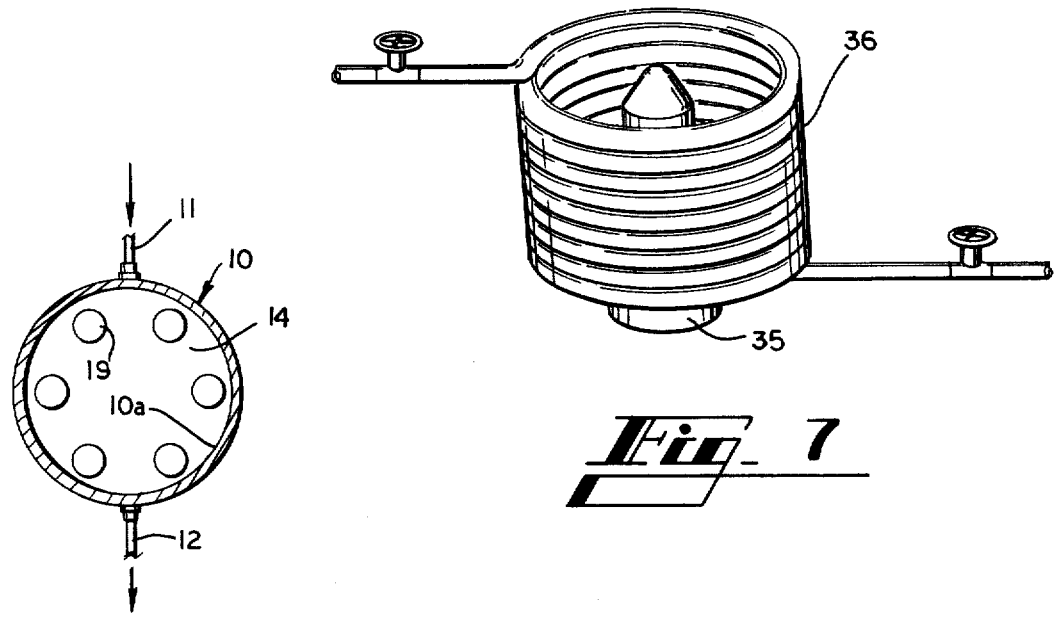
Fig. 2
Fig. 7

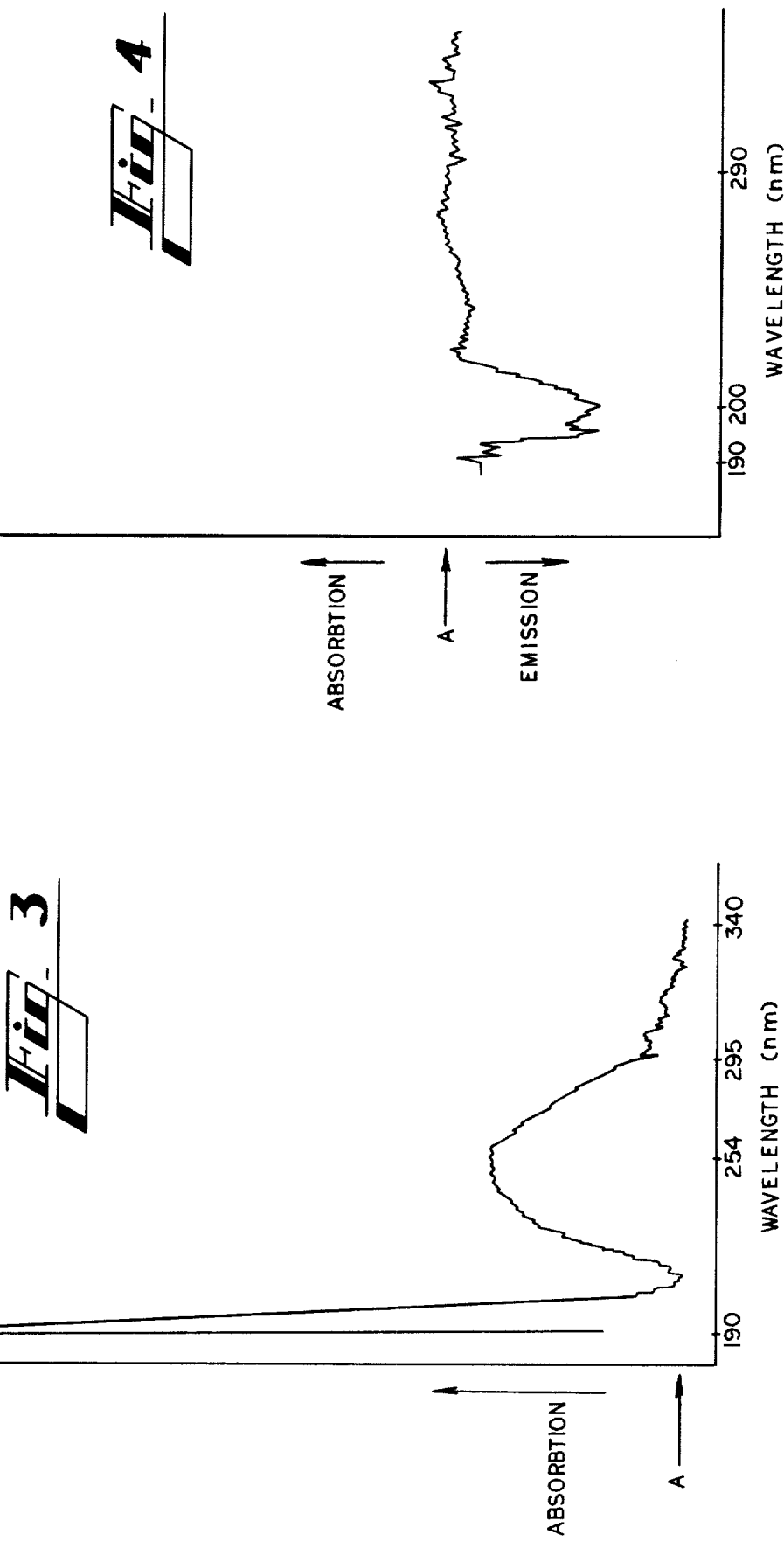

ACTIVATED OXYGEN PRODUCT AND WATER TREATMENT USING SAME

This application is a continuation-in-part of copending application Ser. No. 645,363, filed Dec. 30, 1975 now U.S. Pat. No. 4,124,467.

This invention relates to an activated oxygen product, and is more particularly concerned with a product obtained by irradiating oxygen with electromagnetic radiation.

It is well known that activated forms of oxygen, such as ozone, are oxidizing agents. Ozone is useful as a germicide, bactericide or general antiseptic. Further, ozone or ozonized air has been used in the purification of water.

The production of ozone has been classically carried out in the prior art by subjecting a stream of air or oxygen to an electric discharge. This means of putting energy into oxygen causes at least some of the atoms of oxygen to combine into ozone. The principal difficulty with the prior art production of ozone is the cost of producing even a low-concentration ozonized air. The cost tends to be prohibitive in large commercial uses such as in the purification of water, because of the electrical power requirements. Classical electrical discharge ozone production also produces nitrous oxide, which is corrosive and must be removed by dryer and filter equipment especially provided for the purpose.

A disadvantage of ozone itself in the treatment of water is that mixing ozone prepared in a conventional manner with water causes an increase in the surface tension of the water. This may be undesirable in the treatment of water where low surface tension is desired, such as in filtration systems, in laundry or other washing systems where detergents are used to lower surface tension, and in swimming pools.

Another disadvantage of ozone in water treatment for disinfection is that it forms substances generally thought to be carcinogens.

The present invention overcomes the above mentioned and other difficulties with the prior art production and utilization of ozone by providing a new activated oxygen product which exhibits the disinfecting properties of ozone but does not share many of the disadvantages of ozone. The product of the invention is produced by irradiating oxygen with electromagnetic radiation having a wavelength less than 200 nanometers. The activated oxygen product thus produced is a significantly better oxidizing agent than ozone, reduces the surface tension of water when mixed therewith, and may be produced at far less cost than classically produced ozone.

Surprising advantageous results are achieved when the product of the present invention is used to treat water according to the method of the invention. When mixed with water, the product of the invention reduces the surface tension of the water, a result exactly opposite to the effect of ozone on water. Low surface tension is especially advantageous in industrial water treatment systems since less power is required to drive the water through a filter. Many such systems, such as cooling towers, require disinfection as well as filtration to prevent any accumulation of organisms or particulate matter that could foul the working parts of the system. The product's combined effect of disinfection plus the lowering of surface tension is beneficial also in laundries and other washing systems where detergents are used to lower surface tension to allow oils and grease to emulsify and be washed away.

When used to treat water for human consumption or for swimming pools, the increased oxidation potential of the activated oxygen product of the present invention provides more effective, efficient disinfection than ozone, and does not produce any of the recognized carcinogens which are produced by ozone and chlorination. If the product of the invention is produced in a polyvinylchloride enclosure, free chlorine is liberated to provide a chlorine residual in the water without separately adding chlorine.

When used to treat waste water from industrial processes or sewage, the high oxidation potential of the product of the invention breaks down highly toxic substances such as cyanides.

Finally, treatment of sea water by mixing with the product of the invention aids in the desalinization process by precipitating manganous ions out of solution as manganese dioxide. Removal of dissolved salts in seawater is accomplished by hyper-filtration through membranes, so that elimination of manganous salts reduces the filtration required. Furthermore, the sea water is disinfected, thereby preventing growth of organisms on the membrane.

The product obtained by irradiation of oxygen or air as described above is an activated form of oxygen, the precise chemical identity of which is not yet known. However, the product can be identified by its properties, which also serve to demonstrate its novelty. In addition to those described above, when irradiation occurs in a polyvinylchloride enclosure and the product is subsequently dissolved in sulphuric acid at a pH of 1.5, the product has an ultraviolet spectrum including emission of photons between approximately 190 and 240 nanometers. When irradiation occurs in a polyvinylchloride enclosure and the product is subsequently dissolved in phosphoric acid at a pH of 1.5, the product has an ultraviolet spectrum including absorbtion at about 195 nanometers and at about 254 nanometers. The product is negatively charged, whereas ozone is positively charged.

These and other features and advantages will become apparent from consideration of the following specification when taken in conjunction with the accompanying drawings in which:

FIG. 1 is a pictorial view of one form of apparatus made in accordance with the present invention for the production of activated oxygen through the use of ultraviolet radiation;

FIG. 2 is a cross-sectional view taken substantially along the line 2—2 in FIG. 1;

FIG. 3 is a representation of an ultraviolet spectrum obtained from a solution in phosphoric acid of the product obtained by irradiating oxygen in a polyvinylchloride enclosure according to the present invention;

FIG. 4 is a representation of an ultraviolet spectrum obtained from a solution in sulfuric acid of the product obtained by irradiating oxygen in a polyvinylchloride enclosure according to the present invention;

FIG. 7 is a pictorial view of apparatus made in accordance with the present invention for the production of activated oxygen through the use of a radio-active source of energy.

Figures 5, 6:
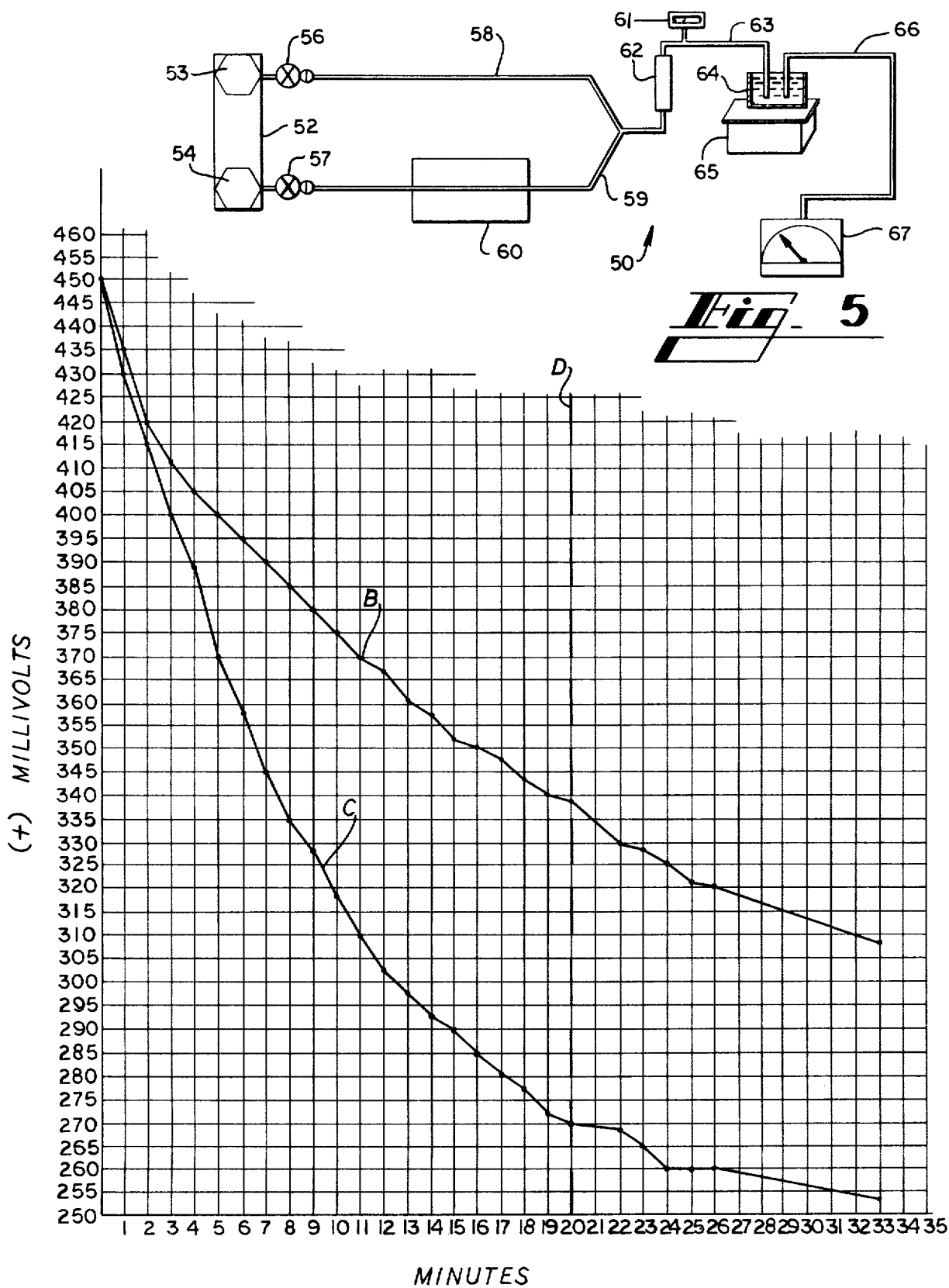
FIG. 5 is a schematic illustration showing an apparatus for testing the oxidation potential of activated oxygen produced according to the present invention.
FIG. 6 is a graphical illustration of results obtained using the apparatus of FIG. 5 for classically produced ozone and activated oxygen produced according to the present invention.

Referring now more particularly to the drawings and to those embodiments of the invention here chosen by way of illustration, a device for producing the product of the invention is shown in FIGS. 1 and 2 of the drawings. Such device includes a casing 10 having an inlet 11 and an outlet 12. The casing 10, with the inlet 11 and outlet 12 defines a path along which air or oxygen moves while being subjected to energy so that activated oxygen or air containing activated oxygen will be discharged from the outlet 12.

Those skilled in the art will understand that oxygen comprises approximately 20% of the volume of air, and that air is frequently used in lieu of pure oxygen when the low concentration of oxygen does not militate against the desired result. Thus, for convenience in discussing the present invention, the term "oxygen" will be discussed without regard to whether the oxygen is in its pure form or is in a dilute form such as in air. When there is an important difference between the result achieved with pure oxygen and the result achieved with a dilute mixture of oxygen, the differences will be discussed in detail. It will be understood that "pure oxygen" when used herein refers to oxygen purified by standard commercial processes.

Returning now to FIG. 1 of the drawings, it will be seen that the casing 10 is substantially cylindrical, and is formed of sheet material so the inside of the casing is open, and the two ends are closed by end walls 14 and 15. Adjacent to the end wall 14, there is a housing 16, and adjacent to the end wall 15 there is a housing 18. The two housings 16 and 18 enclose appropriate wiring and a plurality of sockets for receiving the electrical connections for a plurality of tubular lamps 19.

The general form of lamps such as the lamps 19 is well known to those skilled in the art, so no detailed showing of the construction is here presented. The lamps are of the type wherein an electric arc is passed from an electrode in one end of a tube to an electrode in the opposite end of the tube. A gas is present within the tube, and the bombardment of the gas by electrons causes the electrons in the atoms of gas to move out to a higher energy level, and to return to their normal energy state, giving up electromagnetic energy as they do so. It is also known by those skilled in the art that different gases surrender their energy in different wavelengths so that a particular wavelength of energy can be obtained through selection of the proper gas to be bombarded.

Besides producing energy in the desired wavelength, it is necessary to provide a tubular envelope for the lamp which will allow the energy to pass through the envelope for utilization outside the envelope. It will be understood that numerous minerals and types of glass are known, one of which can be selected to be transparent to the desired wavelength of energy.

With this background, attention is again directed to FIGS. 1 and 2 of the drawings. The object of the device is to admit oxygen through the inlet 11 and allow the oxygen to traverse the casing 10 while the oxygen is bombarded by energy from the lamps 19; then, the resulting activated oxygen is discharged through the outlet 12. The desired activated oxygen product is obtained with electromagnetic radiation having a wavelength less than about 200 nanometers (nm). Radiation within this wavelength range will be produced, for example, when the tubes of the lamps 19 are filled with deuterium, which produces a spectrum having peak energy at about 155 nanometers (nm), which will readily pass through a tube made of fluorite glass.

The casing 10 has a plurality of lamps 19 extending therethrough, parallel to the axis of the cylindrical casing. As here shown, there are six lamps generally equally spaced around a circle. While the precise number of lamps is not important, the object is to provide enough lamps to give the desired energy input for the apparatus, and to have generally uniform energy distribution throughout the casing 10 so all oxygen will receive the required amount of energy to make the change from molecular oxygen to the activated oxygen product of the present invention; for some applications, a single lamp 19 has been found to be sufficient. To assure greater utilization of the energy from the lamps 19, the interior wall 10$a$ of the casing 10 may be specular aluminum. The specular quality causes the energy to be reflected inwardly for greater conversion of oxygen to activated oxygen, and the use of aluminum prevents corrosion of the casing by the resulting activated oxygen.

When the lamps 19 are made of fluorite glass and the tube is filled with deuterium gas, passing an electric arc through the tube will produce energy having a wavelength of about 100 nm, and the fluorite glass tube is virtually transparent to this particular wavelength. As a result, energy having a wavelength of about 100 nm will be propagated from each of the lamps 19 and will be reflected when it engages the specular surface of the casing 10. Oxygen passed through the casing 10 under these conditions will be bombarded by the energy and will be changed from molecular oxygen to the activated oxygen product.

While the above discussion has been directed to means for obtaining the maximum amount of the activated oxygen in any given volume of oxygen, it is sometimes desirable to produce less of the activated oxygen for a particular end use, for example. To reduce the percentage of the activated oxygen produced, it has been found that xenon gas used in lieu of deuterium will produce an energy wavelength that will provide less of the activated oxygen; and, it will be readily understood that mixtures of xenon and deuterium will produce varying amounts of the activated oxygen depending on the proportions. Further, it is known that calcite and sapphire transmit energy in the ultraviolet range of frequencies, and can be used instead of fluorite as the tubular enclosure forming the lamps 19 when the energy being utilized to create the activated oxygen is in the ultraviolet range. Other materials which are found to be substantially transparent to energy at the wavelengths here disclosed are ultrapure silica, and mixtures of ultrapure silica with fluorite or calcite.

It has been found that the concentration of activated oxygen in a given flow of oxygen or air through an apparatus such as is shown in FIG. 1 varies with the diameter of the casing 10, and that there is an optimal diameter for each lamp configuration. For instance, when a single lamp according to the invention is positioned at the center of a 36 inch long casing, a higher concentration of activated oxygen is obtained when the casing has a diameter of 4 inches than when the casing diameter is either 2 inches or 6 inches. An optimum diameter exists because at smaller radii a particular flow rate does not allow the oxygen to remain within the casing long enough to absorb sufficient electromagnetic radiation, and because at larger radii the percentage of photons of electromagnetic radiation not absorbed by the oxygen within the casing is related to the inverse square of the distance from the source of the radiation. Thus, for casing diameters greater than the optimum size, the intensity of radiation near the casing wall is too small to produce a high concentration of activated oxygen near the casing wall.

It has also been found that if the inner surface of the casing 10 is polyvinylchloride, free chlorine gas is liberated from the polyvinylchloride to mix with the activated oxygen product of the invention. Thus, in communities which require a certain residual level of free chlorine in water supplies or swimming pools, the residual chlorine level may be achieved using an apparatus for producing the product of the invention without separately adding chlorine. When a polyvinylchloride casing is used in order to produce chlorine, the diameter of the casing must be such that the inner wall 10a of the casing 10 is near enough to the lamp or lamps within the casing to receive sufficient electromagnetic energy to release the desired amount of chlorine.

In certain situations, on the other hand, disinfection of water is required without the presence of any residual chlorine. This is true in fish hatcheries, since chlorine is highly toxic to fish. In order to produce the product of the invention entirely free of chlorine for use as a disinfectant, the casing 10 may be made of a material which will not liberate chlorine when irradiated with electromagnetic radiation having a wavelength less than 200 nm. Alternatively, the inner surface of a polyvinylchloride casing may be shielded by such a non-chlorine-liberating material to prevent any liberated chlorine from mixing with the activated oxygen product.

Thus, two factors influence the selection of the size of the casing and the distance of the inner walls of the casing from the lamps 19 or other source of electromagnetic energy, whether the casing be cylindrical as shown in FIG. 1 or some other shape. These factors are the effects of casing size on the concentration of activated oxygen and on the liberation of chlorine. When it is desired to produce a mixture of activated oxygen and free chlorine, the dimensions of the casing may be selected to obtain the optimum balance of activated oxygen production and chlorine liberation from the walls of a polyvinylchloride casing.

The precise nature of the activated oxygen product produced by irradiation of oxygen with electromagnetic radiation of wavelength less than 200 nm is not known. However, the presence of the product can be confirmed by its chemical and spectral properties.

For instance, the product has unique spectra when dissolved in sulfuric or phosphoric acid. The ultraviolet spectrum of the product dissolved in sulfuric acid at pH 1.5 is shown in FIG. 4 from 190-340 nm. The spectrometer baseline for water is marked A. As shown in FIG. 4, an apparent emission of photons (possibly chemoluminescence) by an unknown entity occurs in the range from 190-240 nm. Absent is any significant absorbtion at 254 nm, where ozone is known to absorb strongly. FIG. 3 shows the spectrum of the product dissolved in phosphoric acid at pH 1.5. Again the spectrometer baseline for water is marked A. No apparent emission occurs, but strong absorbtion by an unknown entity occurs at about 195 nm. In the phosphoric acid solution, the classical ozone absorbtion at 254 nm does occur.

Another important and unexpected property of the activated oxygen product of the invention is that the product is a significantly stronger oxidant than ozone. The comparative oxidation potentials of classical ozone produced with an electric arc and the product of the present invention on tap water were measured using a testing apparatus shown diagrammatically in FIG. 5. An air compressor 52 operates two diaphrams 53 and 54 having separate flow control valves 56 and 57, respectively. Compressed air passing from valve 57 into a treatment line 59 passes through a treatment apparatus 60, which is alternately a device as described above for producing the product of the present invention, and then a corona discharge apparatus for producing classical ozone. In each case the electrical input to the lamps 19 or the corona discharge apparatus is variable to enable control of the concentration of activated oxygen product or ozone being produced. To further control the concentration, the treated air is mixed with diluting air from a dilution line 58, fed through valve 56, in sample line 63, which contains a flow meter 62 and an oxidant concentration meter 61. The treated and diluted air is passed into a beaker 64 of tap water where it is mixed by the action of a magnetic stirrer 65 and dissolved. The valves 56 and 57 and the intensity of oxidant production by the apparatus 60 are controlled to give a treated air flow of about one liter per minute and an oxidant concentration of about 1 ppm for each type of treatment apparatus 60. A probe 66 of an oxidation/reduction potential meter 67 is placed in the beaker 65 to measure the millivolt change in the water's potential during treatment.

The results of testing using the apparatus shown in FIG. 5 are shown in FIG. 6 for tap water having an initial potential of 450 millivolts. The curve marked B shows the change in potential brought about by classically produced ozone, and the curve marked C shows the change brought about by the same concentration of the product of the invention. In both cases the treatment apparatus was shut down after 20 minutes, marked by the dashed line D. The results clearly show that the product of the invention is a significantly stronger oxidant than ozone. Thus, the product of the invention is a stronger disinfectant, and will break down industrial wastes such as cyanides which have hitherto created troublesome disposal problems because of damage to the environment.

The effect of mixing the product of the present invention with water on the surface tension of the water has been tested and found to be opposite to the effect of conventionally produced ozone. The test procedure included placing 150 ml samples of distilled water into glass containers and obtaining baseline surface tension measurements. Subsequently, a sample was poured through an ozone-rich atmosphere which was created by electric arcs. Measurements after exposure to the classical ozone thus generated showed that the surface tension of the water had increased 8.3 dynes/cm. Activated oxygen produced according to the present invention was blown over another sample while the sample was being poured directly over a lamp emitting ultraviolet radiation in the 150 to 200 nm range. Measurements after this exposure showed that the surface tension of the water decreased 29.2 dynes/cm.

The above-described difference in effect on surface tension of water is believed to be attributable to the difference in the charge on classical ozone as compared to the charge on the activated oxygen product of the present invention. In order to compare the electric charge on the two substances, an electrostatic meter (Model WSM-2950, Western Static, Inc.) was connected to sample line 63 of the apparatus of FIG. 5. A 1 ppm concentration of the product of the invention, flowing at 1.2 liters per minute, was measured at 50 volts negative. The same concentration and flow of ozone produced by the corona discharge apparatus was measured at 1250 volts positive.

The creation of carcinogens during disinfection of water for human consumption and bathing in swimming pools has become a major concern. Both chlorination of water and treatment with classically produced ozone create substances which are recognized as being potentially carcinogenic. However, when the product of the invention was combined with substances often found in swimming pool water, such as hair tonic, suntan lotion, deodorant and urine, none of the carcenogenic substances that have been associated with water treated with chlorine or with classically produced ozone was produced.

The absence of carcinogen production in water treatment using the product of the invention is particularly important for large scale industrial applications where waste water is discharged into streams, rivers and lakes. Concern over carcinogen levels and the death of aquatic life has led government authorities to severely restrict the amounts of chlorine that may be discharged into streams, rivers and lakes. In a case, for example, where the water used in a power plant cooling tower can no longer be treated by the heavy chlorination commonly used, treatment using the activated oxygen product of the invention may be effectively used to disinfect the water, so that the regulations regarding chlorine discharge into natural bodies of water may be satisfied.

It has further been found that the product of the invention, when bubbled through seawater, removes manganese from the seawater by precipitating manganese dioxide ($MnO_2$) as a sludge. This is in contrast to the effect of classically produced ozone, which forms soluble permangate when mixed with seawater. The seawater is, of course, also disinfected by treatment with the product of the invention. Such treatment by the product of the invention would reduce the amount of hyper-filtration needed to desalinize the seawater, and would prevent growth or organisms on the hyper-filtration membranes used in desalinization.

Looking now to FIG. 7 of the drawings, it will be noted that the present invention also contemplates the use of higher energy, or shorter wavelength, radiation. FIG. 7 illustrates the use of a radioactive source of energy, the radiation being in the form of gamma rays. Because of the inherently high energy output from a radioactive source, it is contemplated that only pure oxygen will be used in the apparatus of FIG. 7, since the energy level will tend to ionize other constituents of a gas mixture so that undesirable compounds are quite likely to form. Also because of the inherently high energy output from a radioactive source, it is contemplated that somewhat "waste" sources will be used. One example of such "waste" source is Cesium 137. In addition, Cobalt 60, Strontium 90, Krypton 85 or other gamma sources can be used.

FIG. 7 illustrates somewhat generally a radioactive source 35, the source 35 being surrounded by a casing 36 through which oxygen is passed. The casing 36 is in the form of a helical tubing wound around the source 35 to provide enough length for the oxygen within the casing 36 to receive the energy required to convert the oxygen to ozone. Since the source 35 will emit high energy radiation, probably in the gamma ray spectrum, the oxygen can be moved through the casing 36 at a relatively high speed; however, if pure oxygen is used, there is no harm in an overdose of energy, which otherwise could produce undesirable nitrogen compounds.

While no particular shielding or other structure is shown in conjunction with the apparatus of FIG. 7, it will be understood that conventional shielding apparatus would be used. The source 35 and the casing 36 can be placed within a shielded enclosure using lead or the like. Alternatively, the entire apparatus can be placed in heavy water, which acts as a moderator between the source 35 and the casing 36. Other physical arrangements will suggest themselves to those skilled in the art.

The difference in wavelength between gamma radiation and the ultraviolet radiation produced by exciting deuterium gas illustrates the fact that a broad range of electromagnetic radiation may be used to irradiate oxygen to produce the activated oxygen product of the present invention. Any electromagnetic radiation of wavelength less than 200 nm is satisfactory so long as the energy is not so great as to disrupt the nucleii of the oxygen atoms. However, it is necessary to irradiate pure oxygen when the wavelength of the radiation utilized is less than about 80 nm, since such radiation breaks down nitrogen molecules and leads to the formation of undesirable nitrogen compounds.

It will of course be understood that the particular embodiments of the invention are here shown by way of illustration only, and other embodiments of the same invention are equally encompassed, as described in the accompanying claims.

What is claimed is:

1. An activated oxygen product, comprising oxygen irradiated using a source of electromagnetic radiation of wavelengths predominantly less than 200 nanometers, said product having the properties of:
   reducing the surface tension of water;
   having an ultraviolet spectrum, measured following irradiation in a polyvinyl chloride enclosure and subsequent dissolving of the product in sulfuric acid at a pH of 1.5, including emission in a frequency range including 200 nanometers;
   having an ultraviolet spectrum, measured following irradiation in a polyvinyl chloride enclosure and subsequent dissolving of the product in phosphoric acid at a pH of 1.5, including absorption at 195 nanometers and at 254 nanometers;
   being negatively charged;
   having a greater oxidation potential than ozone; and
   forming manganese dioxide with sea water.

2. A method of disinfecting water, comprising the steps of:
   irradiating oxygen using a source of electromagnetic radiation having predominant wavelengths less than about 155 nm to form an activated oxygen product, said product having the properties of:
   reducing the surface tension of said water;
   having an ultraviolet spectrum, measured following irradiation in a polyvinyl chloride enclosure and subsequent dissolving of the product in sulfuric acid at a pH of 1.5, including absorbtion at 195 nanometers and at 254 nanometers;

being negatively charged;

having a greater oxidation potential than ozone; and forming manganese dioxide with sea water; and mixing said activated oxygen product with said water.

3. The method of claim 2 further comprising the step of irradiating said water with said electromagnetic radiation while mixing said irradiated activated oxygen product with said water.

4. The method of claim 2 wherein said irradiation step comprises irradiating pure oxygen with gamma radiation.

5. A method of reducing the surface tension of water, comprising the steps of:
   irradiating oxygen using a source of electromagnetic radiation having predominant wavelengths less than about 155 nm to form an activated oxygen product; and
   mixing said activated oxygen product with said water.

6. A method of removing manganese from seawater, comprising the steps of:
   irradiating oxygen using a source of electromagnetic radiation having predominant wavelengths less than 200 nm to form an activated oxygen product; and
   mixing said activated oxygen product with said seawater to precipitate manganese dioxide.

7. A method of producing an activated oxygen product mixed with chlorine, comprising the step of:
   irradiating oxygen in a polyvinylchloride enclosure with electromagnetic radiation having a wavelength less than 200 nm.

8. A method of disinfecting water comprising the steps of:
   irradiating oxygen with electromagnetic radiation in a polyvinylchloride enclosure to form a mixture of an activated oxygen product and free chlorine; and
   mixing said mixture of activated oxygen product and chlorine with said water.

9. An apparatus for producing a mixture of an activated oxygen product and free chlorine comprising:
   a polyvinylchloride enclosure;
   a source of electromagnetic radiation having a wavelength less than 200 nm within said enclosure;
   means for introducing oxygen into said enclosure; and
   means for discharging a mixture of activated oxygen product and free chlorine from said enclosure.

10. The apparatus of claim 9 wherein the inner surfaces of said enclosure are sufficiently near to said source to receive sufficient radiation to liberate a predetermined amount of free chlorine from said polyvinylchloride.

11. An activated oxygen product mixed with chlorine, comprising oxygen irradiated in a polyvinyl chloride enclosure with electromagnetic radiation having a wavelength less than 200 nm.

12. An activated oxygen product, comprising oxygen irradiated using a source of electromagnetic radiation of wavelengths predominantly less than about 155 nanometers, said product having the properties of:
   reducing the surface tension of water;
   having an ultraviolet spectrum, measured following irradiation in a polyvinyl chloride enclosure and subsequent dissolving of the product in sulfuric acid at a pH of 1.5, including emission in a frequency range including 200 nanometers;
   having an ultraviolet spectrum, measured following irradiation in a polyvinyl chloride enclosure and subsequent dissolving of the product in phosphoric acid at a pH of 1.5, including absorption at 195 nanometers and at 254 nanometers;
   being negatively charged;
   having a greater oxidation potential than ozone; and
   forming manganese dioxide with sea water.

13. The product of claim 12, wherein said oxygen is irradiated using a source comprising ionized gas selected from the group consisting of deuterium, and mixtures of deuterium and xenon.

14. The product of claim 12, wherein said oxygen is irradiated with gamma radiation.

* * * * *